United States Patent [19]

Wahlstrom

[11] Patent Number: 5,375,615
[45] Date of Patent: Dec. 27, 1994

[54] DENTAL FLOSS TOOL

[76] Inventor: Donald W. Wahlstrom, 3770 S. 4745 West St., West Valley City, Utah 84120

[21] Appl. No.: 194,007
[22] Filed: Feb. 9, 1994
[51] Int. Cl.$^5$ .............................................. A61C 15/00
[52] U.S. Cl. .................................. 132/325; 132/324
[58] Field of Search .............. 132/323, 324, 325, 326, 132/327

[56] References Cited

U.S. PATENT DOCUMENTS

| | | | |
|---|---|---|---|
| 2,577,597 | 12/1951 | Wright | 132/326 |
| 3,519,004 | 7/1970 | Foster. | |
| 3,525,462 | 8/1970 | Freedman. | |
| 3,759,272 | 9/1973 | Di Vincenti. | |
| 3,814,114 | 6/1974 | Roberts | 132/325 |
| 3,913,597 | 10/1975 | Day | 132/324 |
| 4,031,909 | 6/1977 | Kelley. | |
| 4,790,336 | 12/1988 | Kuo | 132/323 |
| 4,995,361 | 2/1991 | Lorenzana et al. | 132/323 |
| 5,020,554 | 6/1991 | Feinberg. | |
| 5,176,157 | 1/1993 | Mazza | 132/325 |
| 5,197,498 | 3/1993 | Stewart | 132/323 |

Primary Examiner—John G. Weiss

[57] ABSTRACT

A tool structure including a container housing a spool of dental floss is provided. A dental floss filament from the spool is directed through the housing and extends through a support rod, wherein a plurality of arcuate legs are provided extending from the support rod and arranged separated relative to one another at an acute angulation. The filament is directed through a first of the legs and extends from an outer distal end of the first leg to a second one of the legs to support dental floss therebetween. A free distal end of the dental floss is secured to a lock fastener mounted to the support rod adjacent the origin of the first and second legs.

4 Claims, 2 Drawing Sheets

DENTAL FLOSS TOOL

BACKGROUND OF THE INVENTION

1. Field of the Invention

The field of invention relates to dental floss tool structure, and more particularly pertains to a new dental floss tool wherein the same is arranged to provide for a filament of dental floss arranged in suspension between spaced legs for use in a dental cleaning procedure.

2. Description of the Prior Art

Dental floss holder and dispenser structure is indicated in the prior art such as in U.S. Pat. Nos. 3,759,272; 5,020,554; 4,031,909; 3,519,004; and 3,525,462.

The instant invention attempts to overcome deficiencies of the prior art by providing for a tool structure maintaining dental floss in an enclosed orientation for the sanitary storage of the dental floss prior to use, whereby a length of dental floss may be dispensed therefrom and suspended between a pair of legs. In this respect, the present invention substantially fulfills this need.

SUMMARY OF THE INVENTION

In view of the disadvantages inherent in the known types of dental floss tools now present in the prior art, the present invention provides a dental floss tool wherein the same is arranged to direct dental floss from a dispensing container for use by an individual. As such, the general purpose of the present invention, which will be described subsequently in greater detail, is to provide a new dental floss tool apparatus and method which has many of the advantages of the prior art listed heretofore and many novel features that result in a dental floss tool apparatus which is not anticipated, rendered obvious, suggested, or even implied by any of the prior art, either alone or in any combination thereof.

To attain this, the present invention provides a tool structure including a container housing a spool of dental floss is provided. A dental floss filament from the spool is directed through the housing and extends through a support rod, wherein a plurality of arcuate legs are provided extending from the support rod and arranged separated relative to one another at an acute angulation. The filament is directed through a first of the legs and extends from an outer distal end of the first leg to a second one of the legs to support dental floss therebetween. A free distal end of the dental floss is secured to a lock fastener mounted to the support rod adjacent the origin of the first and second legs.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new dental floss tool apparatus and method which has many of the advantages of the prior art listed heretofore and many novel features that result in a dental floss tool apparatus which is not anticipated, rendered obvious, suggested, or even implied by any of the prior art, either alone or in any combination thereof.

It is another object of the present invention to provide a new dental floss tool which nay be easily and efficiently manufactured and marketed.

It is a further object of the present invention to provide a new dental floss tool which is of a durable and reliable construction.

An even further object of the present invention is to provide a new dental floss tool which is susceptible of a low cost of manufacture with regard to both materials and labor, and which accordingly is then susceptible of low prices of sale to the consuming public, thereby making such dental floss tools economically available to the buying public.

Still yet another object of the present invention is to provide a new dental floss tool which provides in the apparatuses and methods of the prior art some of the advantages thereof, while simultaneously overcoming some of the disadvantages normally associated therewith.

It is a further object of the present invention to provide a new dental floss tool structure including a container housing a spool of dental floss and wherein a dental floss filament from the spool is directed through the housing and extends through a support rod, wherein a plurality of arcuate legs are provided extending from the support rod and arranged separated relative to one another at an acute angulation.

Still yet another object of the present invention is to provide a new dental floss tool wherein a free distal end of the dental floss is secured to a lock fastener mounted to a support rod adjacent the origin of first and second arcuate legs extending from the support rod.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
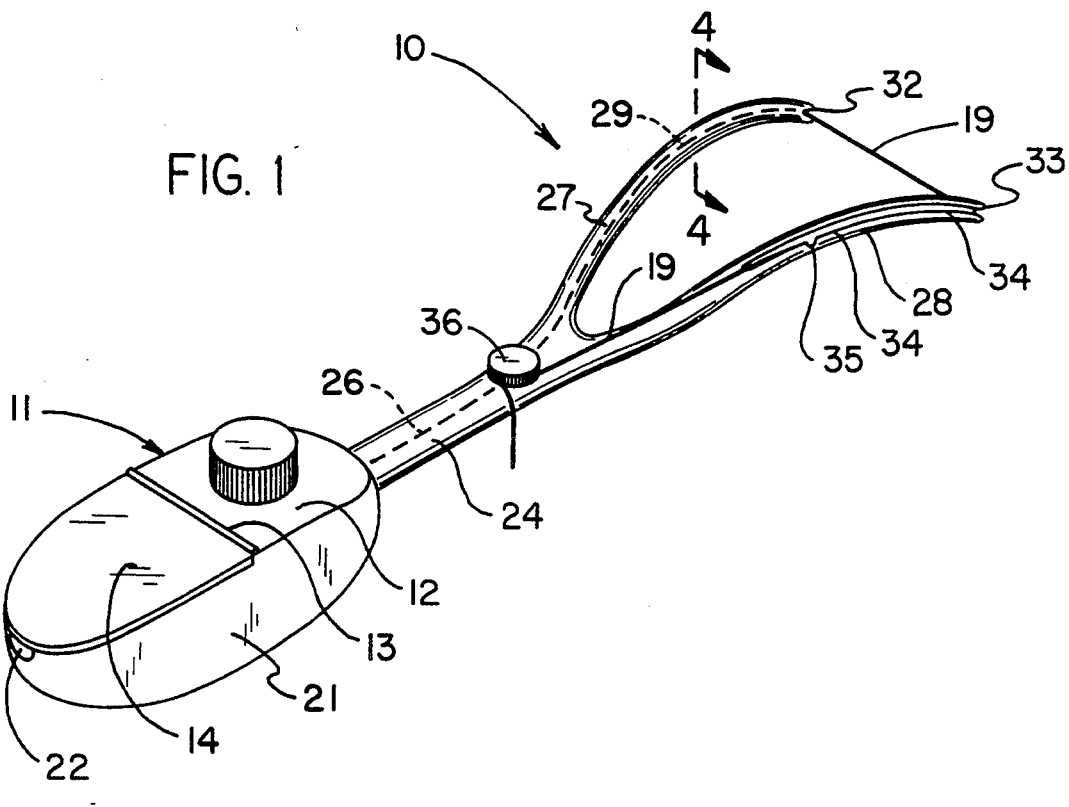
FIG. 1 is an isometric illustration of the invention.

With reference now to the drawings, and in particular to FIGS. 1-4 thereof, a new dental floss tool embodying the principles and concepts of the present invention and generally designated by the reference numeral 10 will be described.

More specifically, the dental floss tool 10 of the instant invention comprises a container 11 having a top wall 12, wherein a lid 14 is secured to the top wall about a hinge 13. The lid 14 is oriented above a container cavity 15 within the container 11. The container cavity 15 includes a cavity floor 16, with an axle 17 extending upwardly from the floor 16 and rotatably mounting a spool 18. The spool 18 supports and releasably contains a dental floss filament 19 which extends circumferentially thereabout.

The container 11 further includes a container bottom wall 20, as well as container side walls 21, a container front wall 22, and a container rear wall 23. The container front wall 22 includes a latch structure for latching the lid 14 to the front wall. The rear wall 23 fixedly mounts a support rod 24 which extends outwardly therefrom. A container conduit 25 is directed through the container from the container cavity 15 and is located medially between the top wall 12 and the container bottom wall 20. The container conduit 25 is in spatial communication with a support rod conduit 26 directed through the support rod 24 to allow at least a portion of the dental floss filament 19 to extend therethrough.

Figure 4:
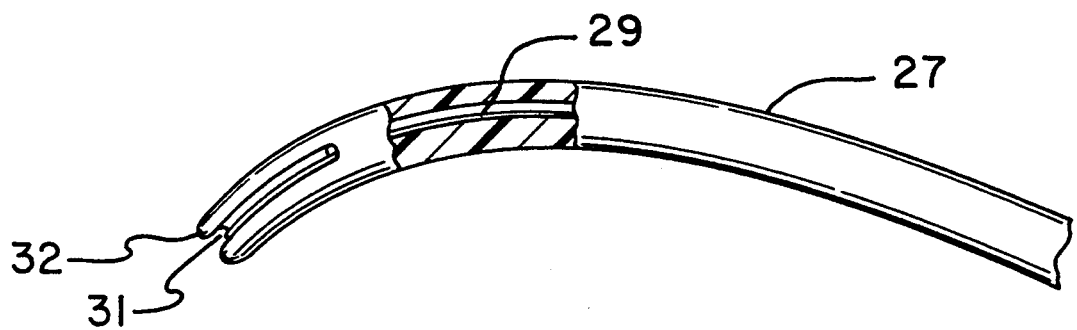
FIG. 4 is an orthographic view, partially in cross section along lines 4—4 of FIG. 1 in the direction indicated by the arrows.

As best illustrated in FIGS. 1 and 4, the support rod 24 continues into arcuate first and second legs 27, 28 which are joined to the support rod 24 at a junction, with the first and second legs being arranged in a coextensive relationship relative to one another and further being oriented at an acute angulation relative to one another. The support rod conduit 26 is directed into communication with a first leg feed conduit 29 extending coextensively through both the first leg and a first leg outermost end 32 into a first leg guide slot 31 directed about the first leg outermost end 32.

A second leg outermost end 33 spaced from the first leg outermost end 31 includes a second guide slot 34 extending therefrom and directed along an outer side wall of the second leg 28. The filament 19 may then be extended between the first and second legs 27, 28 to form a span thereacross suitable for subsequent use thereof by a person for flossing and the like.

Figure 2:
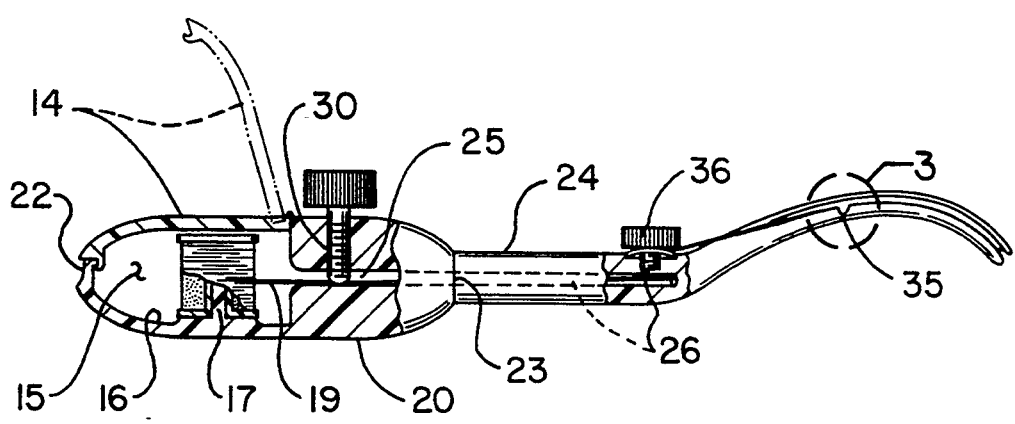
FIG. 2 is a side elevation view, partially in cross section, of the invention.
Figure 3:
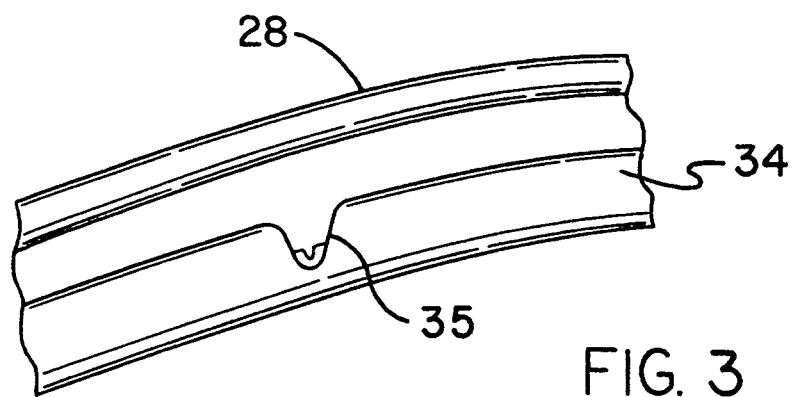
FIG. 3 is an enlarged orthographic view of the curing blade mounted to a second leg of the invention, as indicated in FIG. 2.

A cutter blade 35 extends over the second guide slot 34 to permit selective cutting and severing of the filament 19 within the second guide slot 34. After such severing, a free distal end of the filament 19 is secured to a lock fastener 36 that is directed into the junction of the first and second legs 27, 28 in their securement to the support rod 24. As best illustrated in FIG. 2, the lock fastener 36 includes an unlabeled threaded fastener threadably engaged to the support rod, with an arcuate member interposed between the threaded fastener and said support rod. By this structure, the filament can be positioned between the arcuate member and the head of the threaded fastener to secure the filament relative to the support rod. Positioning the cutter blade 35 between the span and the lock fastener 36 allow for conservation of the filament 19 and further allows for the placement of the lock fastener closer to the legs 27, 28, thereby reducing the length of tensioned filament to result in a more tension within the span. Because of the recessed mounting of the cutter blade 35, accidental engagement with the blade by a user is precluded.

As illustrated in FIG. 2, a lock fastener 30 directed through the container top wall 12 extends into communication with the container conduit 25 to arrest and engage the filament 19 therewithin.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A dental floss tool comprising:
    a container, the container having a top wall spaced from a bottom wall, spaced side walls, a front wall, and a rear wall, a lid, and a hinge pivotally connecting the lid to the top wall, with the lid extending beyond the top wall and over the bottom wall, with the container having a container cavity between the lid and the container bottom wall, the cavity having a cavity floor;
    an axle mounted to the cavity floor;
    a spool wound about the axle;
    a support rod integrally mounted to the container rear wall;
    a first arcuate leg and a second arcuate leg intersecting the support rod at a junction, with the first leg and the second leg concentrically oriented about the junction, with the junction integral to the support rod and spaced from the rear wall, and the first leg having a first leg outermost end, and the second leg having a second leg outermost end; and, a filament wound about the spool, the filament extending from the spool about the first leg outermost end and the second leg outermost end to form a span thereacross;

wherein the container includes a container conduit between the top wall and the bottom wall in communication with the cavity, and a support rod conduit directed through the support rod in communication with the container conduit, and a first leg feed conduit directed through the first leg coextensively thereof in communication with the support rod conduit, with the filament directed from the spool through the container conduit, the support conduit, and the first leg feed conduit.

2. The tool as set forth in claim 1, wherein the first leg outermost end includes a first leg guide slot positioning the filament therewithin, and the second leg includes a second leg guide slot directed about the second leg outermost end and along an exterior surface of the second leg receiving the filament therealong; and further comprising a lock fastener directed into the support rod adjacent the junction to secure the filament to the support rod between the support rod and the lock fastener, said lock fastener comprising a first threaded fastener threadably engaged to said support rod, with an arcuate member interposed between said first threaded fastener and said support rod, whereby said filament is received between said arcuate member and a head of said first threaded fastener to secure said filament relative to said support rod.

3. The tool as set forth in claim 2, and further comprising a further lock fastener directed through the top wall intersecting the container conduit to engage and secure the filament within the container conduit to arrest movement of the filament through the container conduit, said further lock fastener comprising a second threaded fastener threadably engaged to said support rod and extending into said support rod conduit so as to capture said filament between said second threaded fastener and a portion of said support rod conduit.

4. A dental floss tool comprising:

a container, the container having a top wall spaced from a bottom wall, spaced side walls, a front wall, and a rear wall, a lid, and a hinge pivotally connecting the lid to the top wall, with the lid extending beyond the top wall and over the bottom wall, with the container having a container cavity between the lid and the container bottom wall, the cavity having a cavity floor;

an axle mounted to the cavity floor;

a spool wound about the axle;

a support rod integrally mounted to the container rear wall;

a first arcuate leg and a second arcuate leg intersecting the support rod at a junction, with the first leg and the second leg concentrically oriented about the junction, with the junction integral to the support rod and spaced from the rear wall, and the first leg having a first leg outermost end, and the second leg having a second leg outermost end;

a filament wound about the spool, the filament extending from the spool about the first leg outermost end and the second leg outermost end to form a span thereacross;

wherein the container includes a container conduit between the top wall and the bottom wall in communication with the cavity, and a support rod conduit directed through the support rod in communication with the container conduit, and a first leg feed conduit directed through the first leg coextensively thereof in communication with the support rod conduit, with the filament directed from the spool through the container conduit, the support conduit, and the first leg feed conduit;

wherein the first leg outermost end includes a first leg guide slot positioning the filament therewithin, and the second leg includes a second leg guide slot directed about the second leg outermost end and along an exterior surface of the second leg receiving the filament therealong;

and further comprising a lock fastener directed into the support rod adjacent the junction to secure the filament to the support rod between the support rod and the lock fastener, said lock fastener comprising a first threaded fastener threadably engaged to said support rod, with an arcuate member interposed between said first threaded fastener and said support rod, whereby said filament is received between said arcuate member and a head of said first threaded fastener to secure said filament relative to said support rod; a further lock fastener directed through the top wall intersecting the container conduit to engage and secure the filament within the container conduit to arrest movement of the filament through the container conduit, said further lock fastener comprising a second threaded fastener threadably engaged to said support rod and extending into said support rod conduit so as to capture said filament between said second threaded fastener and a portion of said support rod conduit; and a cutter blade mounted to said second leg proximal to said second guide slot to permit selective cutting to said second guide slot to permit selective cutting of said filament.

* * * * *